US009074247B2

(12) United States Patent
Su et al.

(10) Patent No.: US 9,074,247 B2
(45) Date of Patent: Jul. 7, 2015

(54) P53 ASSAY FOR A URINE TEST FOR HCC SCREENING

(71) Applicants: Ying-Hsiu Su, Audubon, PA (US); Selena Y. Lin, West Chester, PA (US)

(72) Inventors: Ying-Hsiu Su, Audubon, PA (US); Selena Y. Lin, West Chester, PA (US)

(73) Assignee: Drexel University, Philadelphia, PA (US)

( * ) Notice: Subject to any disclaimer, the term of this patent is extended or adjusted under 35 U.S.C. 154(b) by 85 days.

(21) Appl. No.: 13/647,991

(22) Filed: Oct. 9, 2012

(65) Prior Publication Data

US 2013/0130244 A1 May 23, 2013

Related U.S. Application Data

(60) Provisional application No. 61/544,119, filed on Oct. 6, 2011.

(51) Int. Cl.
*C12Q 1/68* (2006.01)
*C07H 21/00* (2006.01)

(52) U.S. Cl.
CPC ............ *C12Q 1/6853* (2013.01); *C12Q 1/6886* (2013.01); *C12Q 2600/156* (2013.01)

(58) Field of Classification Search
USPC ................ 435/6.1, 91.2; 536/22.1, 23.1, 24.3
See application file for complete search history.

(56) References Cited

U.S. PATENT DOCUMENTS

2003/0143600 A1* 7/2003 Gocke et al. ...................... 435/6
2010/0203532 A1* 8/2010 Makrigiorgos ................... 435/6
2013/0149695 A1* 6/2013 Lee et al. ........................... 435/5

OTHER PUBLICATIONS

Ahern H. The Scientist 9 (15) : 20 (1995).*
Crockett et al., Fluorescein-Labeled Oligonucleotides for Real-Time PCR: Using the Inherent Quenching of Deoxyguanosine Nucleotides. Analytical Biochemistry 290 : 89 (2001).*
Dominguez et al., Wild-type blocking polymerase chain reaction for detection of single nucleotide minority mutations from clinical specimens. Oncogene 24 :6380 (2005).*
Gundry et al. Base-pair neutral homozygotes can be discriminated by calibrated high-resolution melting of small amplicons. Nucleic Acids Research 36 (10) :3401 (2008).*
Huang et al., Codon 249mutation in exon 7 of p53 gene in plasma DNA : maybe a new early diagnostic marker of hepatocellular carcinoma in Qidong risk area, China. World Journal of Gasteroenterology 9 (4) :692 (2003).*
Klassen et al., Improved real-time detection of the H63D and S65C mutations associated with hereditary hemochromatosis using a SimpleProbe assay format. Clinical Chemistry and Laboratory Medicine 46(7) : 985 (2008).*
Arjomand-Nahad et al., Genotyping of the triallelic variant G2677T/A in MDR1 using LightCycler with locked-nucleic-acid-modified hybridization probes. Analytical Biochemistry 334 :201 (2004).*
Oldenberg et al., Selective Amplification of Rare Mutations Using Locked Nucleic Acid Oligonucleotides that Competitively Inhibit Primer Binding to Wild-Type DNA. J. of Investigative Dermatology 128 :398 (2008).*
Ren et al., Rapid and sensitive detection of hepatitis B virus 1762T/1764A double mutation from hepatocellular carcinomas using LNA-mediated PCR clamping and hybridization probes. J. of Virological Methods 158 :24 (2009).*
Su et al. Detection of K-ras mutation in urine of patients with colorectal cancer. Cancer Biomarker 1 :177 (2005).*
Gilad et al., Serum MicroRNAs Are Promising Novel Biomarkers. PLos One 3(9) : e3148 (2008).*
Shekhtman et al. Optimization of Transrenal DNA Analysis:Detection of Fetal DNA in Maternal Urine. Clinical Chemistry 55 (4) : 723 (2009).*
Anker et al., "Circulating nucleic acids in plasma or serum," Clin. Chim. Acta, Nov. 2001, 313(1-2), 143-146.
Chan et al., "Cell-free nucleic acids in plasma, serum and urine: a new tool in molecular diagnosis," Ann. Clin. Biochem., Mar. 2003, 40(2), 122-130.
Diehl et al., "Circulating mutant DNA to assess tumor dynamics," Nat Med., Technical Report, Sep. 2008, 14(9), 985-990.
El-Serag et al., "Rising Incidence of Hepatocellular Carcinoma in the United States," New Engl. J. Med., Mar. 1999, 340(10), 745-750.
Hsu et al., "Mutational hot spot in the p53 gene in human hepatocellular carcinomas," Nature, Apr. 1991, 350(6317), 427-428.
Klintmalm G. B., "Liver Transplantation for Hepatocellular Carcinoma: A Registry Report of the Impact of Tumor Characteristics on Outcome," Ann. Surg., Oct. 1998, 228(4), 479-490.
Kwoh et al., "Target amplification systems in nucleic acid-based diagnostic approaches," Am. Biotechnol. Lab., Oct. 1990, 8(13), 14-25.
Kwoh et al., "Transcription-based amplification system and detection of amplified human immunodeficiency virus type 1 with a bead-based sandwich hybridization format," Proc. Natl. Acad. Sci. USA, Feb. 1989, 86(4), 1173-1177.
Lichtenstein et al., "Circulating Nucleic Acids and Apoptosis," Ann. NY Acad. Sci., Sep. 2001, vol. 945, 239-249.
Lin et al., "A Locked Nucleic Acid Clamp-Mediated Polymerase Chain Reaction Assay for Detection of a P53 Codon 249 Hotspot Mutation in Urine," J. Mol. Diagn., Sep. 2011, 13(5), 474-478.
Lizardi et al., "Exponential Amplification of Recombinant-RNA Hybridization Probes," BioTechnology, Oct. 1988, 6(10), 1197-1202.
Malek et al., "Nucleic Acid Sequence-Based Amplification (NASBA™)," Methods Mol. Biol., 1994, vol. 28, Chapter 36, 253-260.

(Continued)

*Primary Examiner* — Ethan C Whisenant
(74) *Attorney, Agent, or Firm* — Baker & Hostetler LLP

(57) ABSTRACT

A rapid and sensitive assay to detect p53 mutations in urine has been developed for use in screening cancer patients. The method uses a locked nucleic acid (LNA) clamp mediated one-step PCR-based assay with a sensitivity of up to a single copy and can be used not only in urine, but also other biological samples. The assay is particularly useful for hepatocellular carcinoma, colon cancer, breast cancer, lung cancer, prostate cancer, ovarian cancer, bladder cancer, lymphoma, and stomach cancer.

7 Claims, 12 Drawing Sheets

(56) References Cited

OTHER PUBLICATIONS

Pathak et al., "Circulating Cell-Free DNA in Plasma/Serum of Lung Cancer Patients as a Potential Screening and Prognostic Tool," Clin Chem., Oct. 2006, 52(10), 1883-1842.

Su et al., "Human Urine Contains Small, 150 to 250 Nucleotide-Sized, Soluble DNA Derived from the Circulation and May Be Useful in the Detection of Colorectal Cancer," J. Mol. Diagn., May 2004, 6(2), 101-107.

Su et al., "Removal of High-Molecular-Weight DNA by Carboxylated Magnetic Beads Enhances the Detection of Mutated K-ras DNA in Urine," Ann. NY Acad. Sci., Aug. 2008, vol. 1137, 82-91.

* cited by examiner

PCR Assay Design
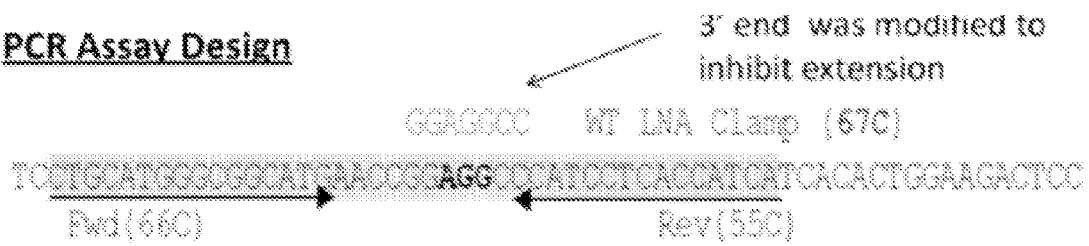
*Red capitalized bases denote LNA
SimpleProbe Design
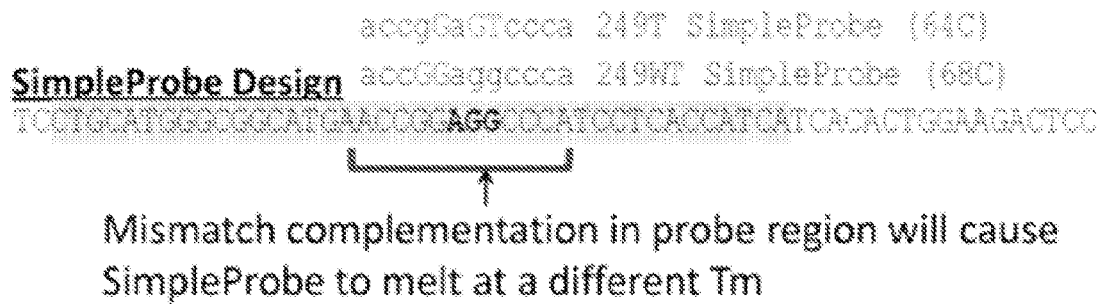
Mismatch complementation in probe region will cause SimpleProbe to melt at a different Tm
FIG. 2

P53 gene real-time PCR Assay 249T and 249WT SimpleProbe Melt Curve Analysis of p53 standards

|    | LNA(-) | LNA(+) |     | LNA(-) | LNA(+) |     | LNA(-) | LNA(+) |     | LNA(-) | LNA(+) |
|----|--------|--------|-----|--------|--------|-----|--------|--------|-----|--------|--------|
| 1  | 1K     | WT     | 1N  | WT     | -      | 11  | 11K    | WT     | 11N | WT     | -      |
| 2  | 2K     | WT     | 2N  | WT     | Mutant | 12  | 12K    | WT     | 12N | WT     | -      |
| 3  | 3K     | WT     | 3N  | WT     | -      | 13  | 13K    | WT     | 13N | WT     | -      |
| 4  | 4K     | WT     | 4N  | WT     | Mutant | 14  | 14K    | WT     | 14N | WT     | -      |
| 5  | 5K     | WT     | 5N  | WT     | -      | 15  | 15K    | WT     | 15N | WT     | -      |
| 6  | 6K     | WT     | 6N  | WT     | -      | 16  | 16K    | WT     | 16N | WT     | -      |
| 7  | 7K     | WT     | 7N  | WT     | -      | 17  | 17K    | WT     | 17N | WT     | Mutant |
| 8  | 8K     | WT     | 8N  | WT     | -      | 18  | 18K    | WT     | 18N | n/a    | Mutant |
| 9  | 9K     | WT     | 9N  | WT     | -      | 19  | 19K    | WT     | 19N | n/a    | n/a    |
| 10 | 10K    | WT     | 10N | Mix    | -      | 20  | 20K    | WT     | 20N | WT     | -      |

| # | Sample | LNA(-) | LNA(+) |
|---|---|---|---|
| 1 | 2K-B | Mutant* | - |
| 2 | 3K-B | WT | - |
|   | 3K-A | WT | - |
|   | 3K HMW | WT | - |
| 3 | 4K-B | WT | Mutant |
| 4 | 5k-B | Mix | Mutant |
|   | 5K-A | WT | - |
|   | 5K HMW | WT | - |
| 5 | 6K-B | Mutant | Mutant |
|   | 6K-A | WT | Mutant |
|   | 6K HMW | WT | - |
| 6 | 7K-B | WT | Mutant |
| 7 | 8K-B | WT | Mutant |
| 8 | 10K-B | Mix | Mutant |
|   | 10K-A | WT | - |
|   | 10K HMW | WT | Mutant |
| 9 | 11K-B | WT | - |
| 10 | 17K-B | WT | Mutant |
|    | 17K-A | WT | - |
|    | 17K HMW | WT | Mutant |
| 11 | 18K-B | WT | - |
|    | 18K-A | WT | Mutant |
|    | 18K HMW | WT | Mutant |
| 12 | 19K-B | Mutant* | - |
|    | 19K-A | Mutant* | - |
|    | 19K HMW | WT | Mutant |
| 13 | 20K-B | WT | Mutant |
|    | 20K-A | Mix | Mutant |

| # | Sample | LNA(-) | LNA(+) |
|---|---|---|---|
| 14 | 21K-B | WT | - |
|    | 21K-A | WT | Mutant |
|    | 21K HMW | WT | - |
| 15 | 25K-B | WT | - |
|    | 25K-A | WT | - |
|    | 25K HMW | WT | - |
| 16 | 26K-B | WT | Mutant |
|    | 26K-A | WT | - |
|    | 26K HMW | WT | - |
| 17 | 27K-B | WT | - |
|    | 27K HMW | WT | - |
| 18 | 1B | WT | - |
|    | 1A | WT | - |
| 19 | 2B | WT | - |
|    | 2A | WT | - |
| 20 | 3B | WT | - |
|    | 3A | WT | - |
| 21 | 4B | WT | - |
|    | 4A | WT | - |
| 22 | 5B | Mutant* | - |
|    | 5A | Mutant* | - |
| 23 | 6B | WT | - |
|    | 6A | WT | - |
| 24 | 7B | WT | - |
|    | 7A | WT | - |
| 25 | 8B | WT | - |
|    | 8A | WT | - |
| 26 | 9B | WT | - |

| # | Sample | LNA(-) | LNA(r) |
|---|---|---|---|
| 27 | 10B | WT | - |
|    | 10A | WT | - |
| 28 | 11B | WT | - |
|    | 11A | - | - |
| 29 | 12B | WT | - |
|    | 12A | - | - |
| 30 | 13B | WT | - |
|    | 13A | - | - |
| 31 | 14B | WT | - |
|    | 14A | WT | - |
| 32 | 7B | n/a | - |
|    | 7A | n/a | - |
| 33 | 16B | n/a | - |
|    | 16A | n/a | - |
| 34 | 13B | n/a | - |
|    | 13A | n/a | Mutant |
| 35 | 9B | n/a | Mutant |
|    | 9A | n/a | - |
| 36 | 4B | n/a | - |
|    | 4A | n/a | - |
| 37 | 8B | n/a | - |
|    | 8A | Mix | - |
| 38 | 10B | n/a | - |
|    | 10A | n/a | - |
| 39 | 11B | n/a | Mutant |
|    | 11A | n/a | - |
| 40 | 16B | n/a | - |
|    | 16A | n/a | - |

Summary p53 screening in urine sample from subjects ranging from normal to diseased liver

|  | # positive | % positive |
|---|---|---|
| Normal (n=15) | 0 | 0% |
| Hepatitis (n=15) | 1 | 6.60% |
| Cirrhosis (n=3) | 0 | 0% |
| HCC (n=40) | 18 | 45% |

FIG. 9

P53 ASSAY FOR A URINE TEST FOR HCC SCREENING

CROSS REFERENCE TO RELATED APPLICATIONS

This application claims the benefit of U.S. Provisional Application No. 61/544,119 filed Oct. 6, 2011 which is hereby incorporated by reference in its entirety.

STATEMENT TO RIGHTS TO INVENTIONS MADE UNDER FEDERALLY SPONSORED RESEARCH OR DEVELOPMENT

This invention was made with Government support under Contract No. RO1 CA125642 awarded by the National Institute of Health (NIH). The Government has certain rights in the invention.

TECHNICAL FIELD

The invention relates to methods for detecting mutations in nucleic acid sequences associated with cancer using samples from biological fluid.

SEQUENCE LISTING

The instant application contains a Sequence Listing which has been submitted in ASCII format via EFS-Web and is hereby incorporated by reference in its entirety. Said ASCII copy, created on Oct. 23, 2012, is named Sequence_Listing_CRF_DXU0615 and is 2,322 bytes in size.

BACKGROUND

Circulating DNA has been identified in biological fluids (Lichtenstein et al., *Ann NY Acad Sci.,* 945:239-49, 2001; Chan et al. *Ann Clin Biochem,* 40:122-30, 2003; Pathak et al. *Clin Chem.* 52:1833-42, 2006; Diehl et al. *Nat Med.* 14:985-90, 2008; Anker et al. *Clin Chim Acta* 313:143-6, 2001.) For example, in urine, two species are seen: a high-molecular-weight (HMW) urine DNA, greater than 1 kb, derived mostly from sloughed off cell debris from the urinary tract; and low-molecular-weight (LMW) urine DNA, approximately 150 to 250 base pairs (bp), derived primarily from apoptotic cells (Su et al. *J Mol Diagn.* 6:101-7, 2004.)

Hepatocellular carcinoma (HCC) is the most frequent cancer in certain parts of the world, and the fifth most cancer common worldwide. Increased incidence is associated with a spread in hepatitis C infections (El-Serag H B, Mason A C., *N Engl J Med* 340 (10):745-50, 1999). Surgical resection is often curative if the disease is localized and diagnosis occurs early (Klintmalm G B., *Ann Surg* 228 (4):479-90, 1998). However, extensive liver impairment associates with a poor prognosis, often due to late diagnosis. Among patients with underlying cirrhotic disease, a progressive increase in alpha-fetoprotein (AFP) and/or in alkaline phosphatase or a rapid deterioration of hepatic function may be the only clue to the presence of cancer.

Mutations in the p53 gene have been associated with approximately 50% of human cancers. In HCC, a G:C to T:A transversion at the codon 249 (249T) is a known "hotspot". (Hsu et al. Nature, 350:377-8, 1991). Current methods of p53 detection such as restriction fragment length polymorphism and PCR-based assays followed by DNA sequencing are time consuming, labor intensive or insensitive. There remains a need for tests to screen for HCC that can detect the disease in early stages and be easily administered. The present invention provides methods for testing for p53 mutations and diseases associated with such types of mutations, e.g., HCC, using biological fluids such as urine. These uses as well as others will be apparent to those skilled in the art from the teachings herein.

SUMMARY

The present description provide methods for detecting a circulating low molecular weight (LMW) nucleic acid sequence from a biological sample comprising comparing an isolated wildtype LMW nucleic acid sequence with the nucleic acid sequence from the biological sample to detect the presence of a mutated LMW sequence, wherein the wildtype LMW sequence is modified at a ribose to prevent amplification of the wildtype sequence in a nucleotide amplification reaction assay.

In certain embodiments, the description herein provide methods where the biological fluid is selected from the group consisting of serum, plasma, and urine.

In certain embodiments, the description herein provide methods where the wildtype LMW nucleic acid sequence is a DNA sequence of 50 nucleotides or less.

In other embodiments, the description herein provide methods where the modification is a methylene bridge connecting a 2'-oxygen and 4'-carbon (locked nucleic acid (LNA) clamp) in the wildtype nucleic acid sequence.

In other embodiments, the methods comprise an additional first step of suppressing amplification of modified wildtype nucleic acid sequence isolated from a biological sample, wherein the suppression using LNA modification is methylene bridge connects a 2'-oxygen and 4'-carbon at a ribose in the wildtype sequence.

In certain embodiments, the description herein provide methods where the sequence is a cancer-associated mutated nucleotide sequence.

In other embodiments, the description herein provide methods where the nucleotide sequence is p53.

In certain embodiments, the description herein provide methods where the biological sample is urine.

In other embodiments, the description herein provide methods where the biological sample is urine of a subject being tested for cancer.

In other embodiments, the description herein provide methods where the cancer is hepatocellular carcinoma, colon cancer, breast cancer, lung cancer, prostate cancer, ovarian cancer, bladder cancer, lymphoma or stomach cancer.

In certain embodiments, the description herein provide methods where the cancer is hepatocellular carcinoma.

In certain embodiments, the description herein provide methods where the mutation is a p53 249T mutation.

In other embodiments, the description herein provide methods comprising an additional first step of isolating a low molecular weight (LMW) nucleic acid from the biological sample prior to comparing the LMW nucleic acid from the urine sample to a wildtype nucleic acid sequence.

In another aspect, the disclosure herein provide kits for detecting a circulating low molecular weight (LMW) mutant nucleic acid sequence from a biological sample comprising (a) locked nucleic acid (LNA) clamp; (b) a primer for amplifying a target sequence comprising nucleotides; and (c) a Fluorescein-labeled oligonucleotide probe, wherein the probe specifically hybridizes to the mutant sequence and emits more fluorescence than it does when it is not hybridized.

In one embodiment, the description herein provide kits wherein the DNA sequence and (c) is a SIMPLEPROBE™.

In one embodiment, the description herein provide kits the low molecular weight (LMW) mutant nucleic acid sequence is p53.

In another aspect, the description herein provide kits for detecting a circulating LMW p53 249T mutant DNA sequences from a urine comprising (a) LNA clamp; (b) a primer for amplifying sequences comprising nucleotides from sequences encoding for codons 248-250; and (c) a Fluorescein-labeled p53 249T oligonucleotide probe, wherein the probe specifically hybridizes to the p53 249T mutant sequence and emits more fluorescence than it does when it is not hybridized.

In one embodiment, the description herein provide kits, wherein (a) consists of SEQ ID NO: 6; (b) consists of SEQ ID NO: 1 and SEQ ID NO: 3; and (c) consists of SEQ ID NO: 4 and SEQ ID NO: 5.

In one embodiment, the description herein provide kits wherein the biological sample is urine.

In one embodiment, the description herein provide kits wherein the biological sample is from a subject being tested for cancer.

In another aspect, the present invention provides methods of identifying a mutated p53 nucleotide sequence from a urine sample of a subject being tested for cancer comprising comparing a low molecular weight (LMW) nucleic acid from the urine sample to a wildtype nucleic acid sequence, wherein the wildtype LNA clamp is modified to prevent amplification of the wildtype sequence in a PCR assay, and wherein the cancer is hepatocellular carcinoma, colon cancer, breast cancer, lung cancer, prostate cancer, ovarian cancer, bladder cancer, lymphoma or stomach cancer. In a preferred embodiment, the cancer is hepatocellular carcinoma.

Other embodiments featured in the methods of the present invention include: wildtype nucleic acid sequences with a chemically modified ribose to prevent amplification of the sequence in a PCR assay, and embodiments where the modification is a methylene bridge connecting the 2'-oxygen and 4'-carbon. In certain other embodiments, the nucleotide sequence is p53. In another embodiment, the method further comprises the step of isolating a low molecular weight (LMW) nucleic acid from the urine sample prior to comparing the LMW nucleic acid from the urine sample to a wildtype nucleic acid sequence.

BRIEF DESCRIPTION OF THE DRAWINGS

FIG. 2 is an illustration of the template sequences designed to assay for the p53 249T mutation. The following sequences are shown: TCCTGCATGGGCGGCATGAACCGGAGGC-CCATCCTCACCATCATCACACTGGAAGAC TCC (SEQ ID NO: 7); GGAGGCC (SEQ ID NO:6); accgGaGTccca (SEQ ID NO:4); accGGaggccca (SEQ ID NO:8)

FIG. 5 illustrates Specificity of the p53 249T mutation assay by using SIMPLEPROBE™ Melting_Curve analysis with 249T probe. The specificity of p53 249T mutation assay was determined by:

(1) reconstitution of 10 CP of plasmid 249T with $10^1$ to $10^7$ CP of WT plasmid in the
  (A) absence WT LNA clamp (249T: WT)
  (B) presence of the WT LNA clamp (249T:WT 1:100, 1:1000)
(2) $10^1$ to $10^7$ CP of plasmid 249T was reconstituted with $10^7$ CP of the WT plasmid DNA in the
  (C) absence WT LNA clamp (249T:WT, 1:10)
  (D) presence of the WT LNA clamp (249T:WT, 1:10, 1:100, 1:1,000)

The specificity was a ratio of 1:1000 of 249T mutant to WT. The LNA suppressed amplification of the WT plasmid up to $10^7$ CP.

FIG. 6 is a table presenting data for p53 mutations in paired HCC (K) and non-HCC (N) tissues. HCC (K) and non-HCC (N) DNA are presented side-by-side and were assayed in the p53 249 mutation assay in the presence (+) and absence (−) of the WT LNA clamp.

Figure 7:
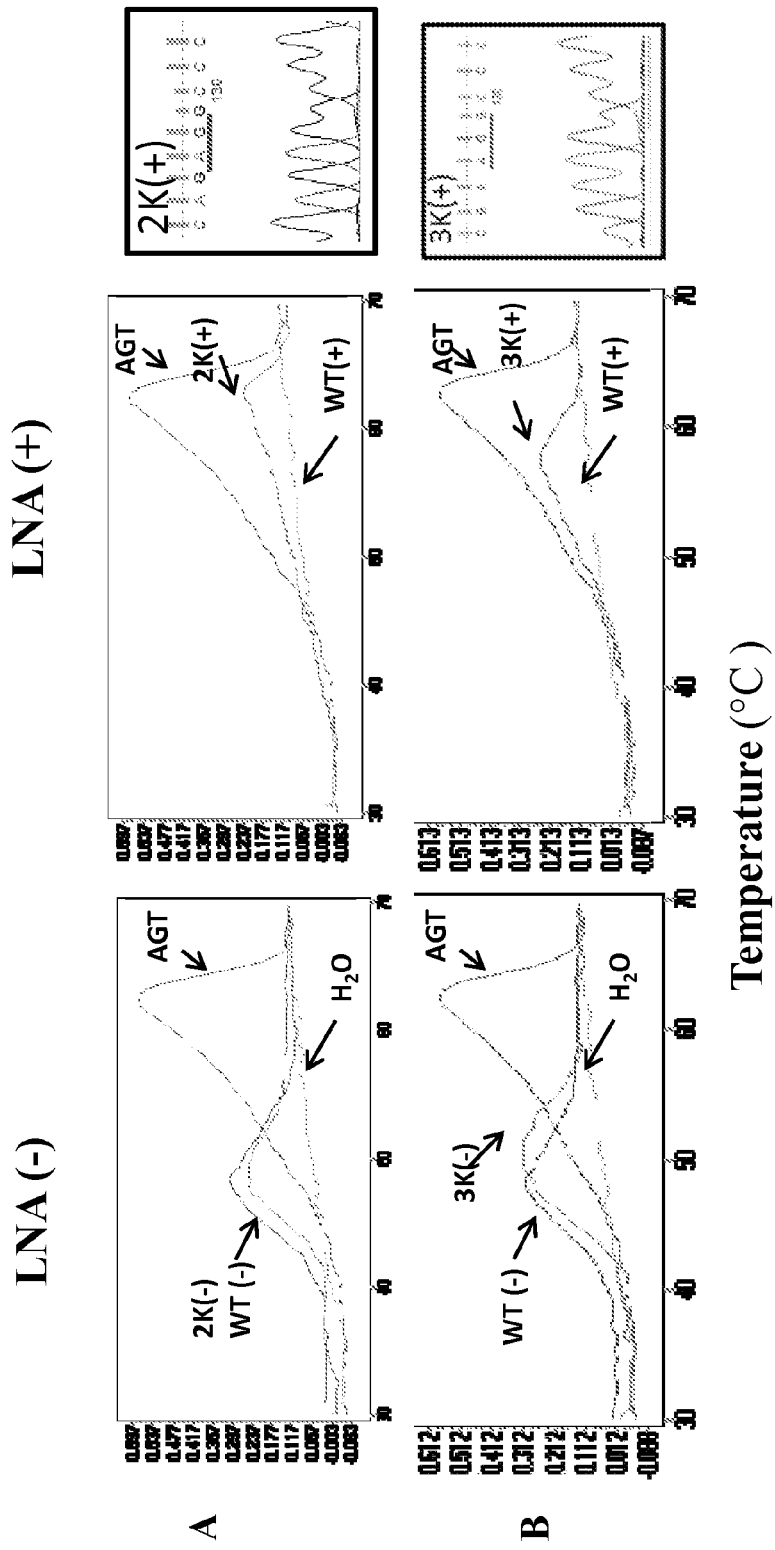
Figure 7:
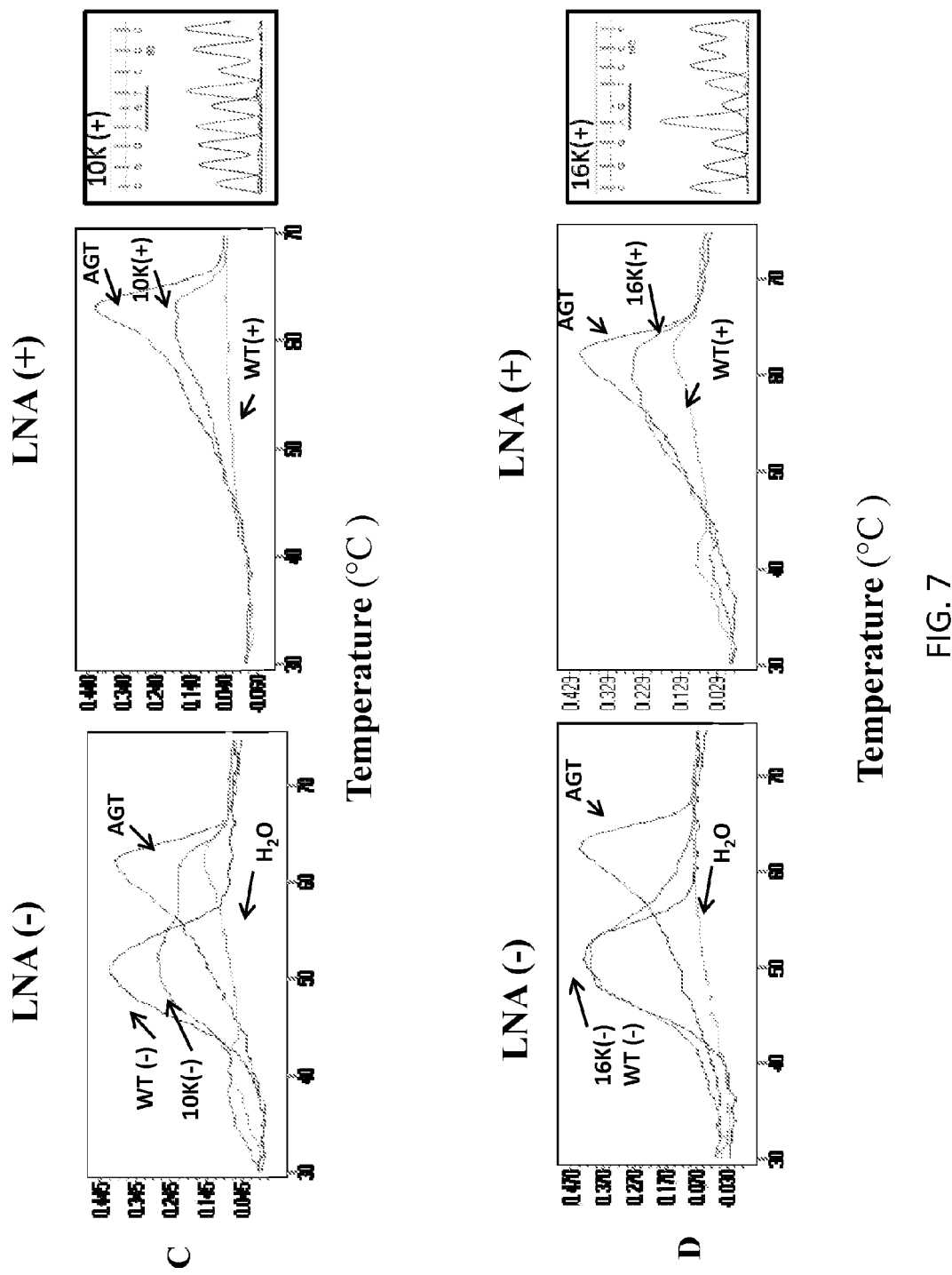
Figure 7:
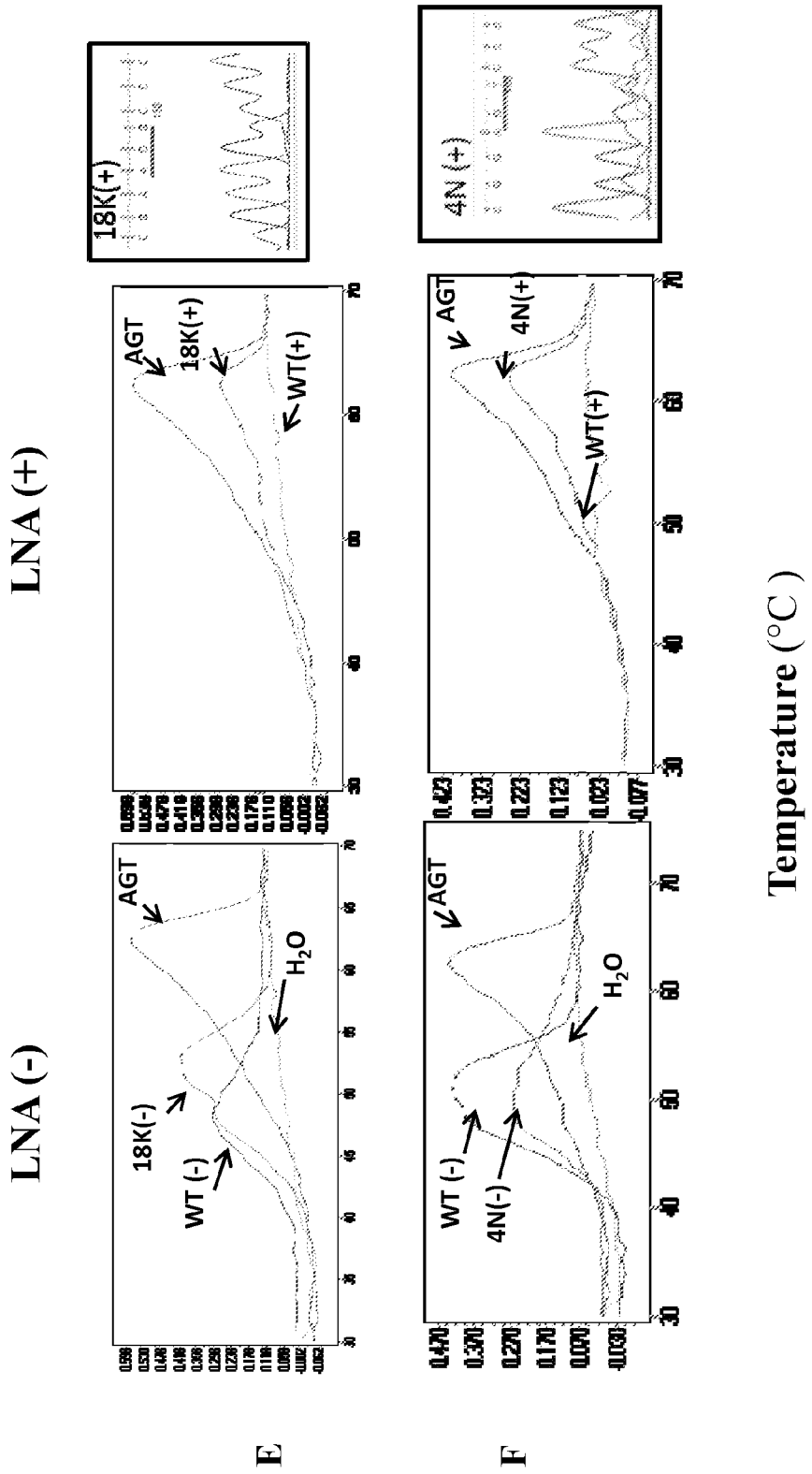

FIG. 7 A-F is melting curve analysis of the tissue DNA detected positive by the p53 249 mutation assay shown in FIG. 6. The PCR products generated in the presence of LNA were cloned into a plasmid and analyzed through DNA sequencing. The DNA sequencing chromatograms showing the mutation site are shown on the right.

FIG. 8 is a table presenting data from 40 HCC LMW DNA sets isolated from urine samples collected before (B) and after (A) surgical removal of HCC tumors.

FIG. 9 is a table presenting data with controls for p53 249 mutation assays using urine DNA sets shown in FIG. 8. LMW urine DNA isolated from normal (n=13), hepatitis (n=15), and cirrhosis (n=3) were used.

DETAILED DESCRIPTION

Unless defined otherwise, all technical and scientific terms used herein have the same meaning as commonly understood by one of ordinary skill in the art pertinent to the methods and compositions described. As used herein, the following terms and phrases have the meanings ascribed to them unless specified otherwise.

The terms "a," "an," and "the" as used herein include plural referents, unless the context clearly indicates otherwise.

The term "nucleic acid" refers to a deoxyribonucleotide (DNA) or ribonucleotide (RNA) and complements thereof. The size of nucleotides are expressed in base pairs "bp". Polynucleotides are single- or double stranded polymers of nucleic acids and complements thereof.

The term "low molecular weight" or LMW nucleic acid refers a nucleic acid, such as DNA, of less than 500 base pairs, usually less than 300 base pairs.

A "locked nucleic acid" LNA is a chemically modified RNA nucleotide whose ribose is modified with a methylene bridge connecting the 2'-oxygen and 4'-carbon.

The term "nucleotide amplification reaction" refers to any suitable procedure that amplifies a specific region of polynucleotides (target) using primers. See generally Kwoh et al., *Am. Biotechnol. Lab.* 8:14 (1990; Kwoh et al., *Proc. Natl. Acad. Sci. USA* 86, 1173-1177 (1989); Lizardi et al., *BioTechnology* 6:1197-1202 (1988); Malek et al., *Methods Mol. Biol.*, 28:253-260 (1994); and Sambrook et al., "Molecular Cloning: A laboratory Manual" (1989)).

A "polypeptide" is a polymer of amino acid residues joined by peptide bonds, whether produced naturally or synthetically. Polypeptides of less than about 10 amino acid residues are commonly referred to as "peptides."

A "protein" is a macromolecule comprising one or more polypeptide chains. A protein may also comprise non-peptidic components, such as carbohydrate groups. Carbohydrates and other non-peptidic substituents may be added to a protein by the cell in which the protein is produced, and will vary with the type of cell. Proteins are defined herein in terms of their amino acid backbone structures; substituents such as carbohydrate groups are generally not specified, but may be present nonetheless.

The terms "amino-terminal" and "carboxyl-terminal" are used herein to denote positions within polypeptides. Where the context allows, these terms are used with reference to a particular sequence or portion of a polypeptide to denote proximity or relative position. For example, a certain sequence positioned carboxyl-terminal to a reference sequence within a polypeptide is located proximal to the carboxyl terminus of the reference sequence, but is not necessarily at the carboxyl terminus of the complete polypeptide.

The term "expression" refers to the biosynthesis of a gene product. For example, in the case of a structural gene, expression involves transcription of the structural gene into mRNA and the translation of mRNA into one or more polypeptides.

The term "antibody," as used herein, refers to immunoglobulin polypeptides and immunologically active portions of immunoglobulin polypeptides, i.e., polypeptides of the immunoglobulin family, or fragments thereof, that contain an antigen binding site that immunospecifically binds to a specific antigen. The term "antibody" also encompasses genetically engineered intact antibodies or fragments such as, for example, chimeric antibodies, humanized antibodies, "Fv" fragments consisting of the variable regions of the heavy and light chains, polypeptides consisting of the light chain variable region, recombinant single chain antibodies in which light and heavy variable regions are connected by a peptide linker ("scFv proteins"), minimal recognition units consisting of the amino acid residues that mimic the hypervariable region, and the like, as well as synthetic antigen-binding peptides and polypeptides.

A "detectable label" is a molecule or atom which can be conjugated to an antibody moiety to produce a molecule useful for diagnosis. Examples of detectable labels include chelators, photoactive agents, radioisotopes, fluorescent agents, paramagnetic ions, or other marker moieties.

The term "effective amount," in the context of treatment of a disease or disorder refers to the amount of such molecule that is sufficient to inhibit the occurrence or ameliorate one or more clinical or diagnostic symptoms of the disease or disorder in a subject. The term "effective regime" refers to a combination of amount of the agent being administered and dosage frequency adequate to accomplish treatment or prevention of the disease or disorder.

Due to the imprecision of standard analytical methods, molecular weights and lengths of polymers are understood to be approximate values. When such a value is expressed as "about" X or "approximately" X, the stated value of X will be understood to be accurate to ±10%.

Described herein are methods providing a sensitive, specific, and noninvasive test for detecting mutations in circulating low molecular weight (LMW) p53 nucleic acid sequences compared to wildtype p53 sequences isolated from a biological samples including body fluid. Any tumor-derived DNA found in a small fraction of LMW urine DNA isolated from patients can be used in the present methods because the of selective amplification of mutated DNA sequences but not wildtype sequence in a nucleotide amplification reaction such as PCR. The methods use a seven nucleotide Locked Nucleic Acid (LNA) clamp designed to suppress the amplification of wildtype sequences of 50 nucleotides or less; amplifying selective p53 templates that contained any mismatches with the LNA clamp. The PCR products were characterized by melting curve analysis. The running time of the assay is less than 2 hours and can be used as a high throughput format for a blood or urine test for screening cancer. As shown in the Examples, the methods are useful for HCC screening. For areas with a low prevalence of the mutation, the screening assay can be combined with other complementary screening tests such as the alpha-fetoprotein blood test and ultrasound imaging.

The invention features three components used in developing the assays. First, an LNA clamp was used to suppress the amplification of a wildtype DNA template, showing that the sensitivity and specificity of the assay could be enhanced. Second, the amplified region in the DNA template was only 41 base pairs. Third, SIMPLEPROBES™ (Roche Applied Sciences, Indianapolis, Ind.) were used to characterize the PCR product by the melting curve analysis. The assay has high sensitivity and specificity. The LNA clamp-mediated PCR assay detects up to a single copy of the mutated sequence with a high specificity ratio of 1:1,000 (0.1%) of mutant to wildtype sequences. The suppression of wildtype template amplification by the LNA clamp is based on the perfect match of the LNA clamp to the wildtype sequences. The base pairing of LNA to DNA exerts higher thermostability than that of DNA to DNA, thus providing a wide range of Tm differences (6-10° C.) between the perfect match and a single base pair mismatch. Based on the Tm difference the inventors optimized the PCR condition to selectively amplify only the mutated sequence and not the wildtype sequence. The result was almost complete suppression of $10^7$ copies of the wildtype sequence when PCR products were detected by the SIMPLEPROBES™. Furthermore, the assay was not only able to detect the 249T mutation but was able to detect any mutation in the region of the LNA clamp.

A biological fluid can comprise, for example, whole tissue, such biopsy sample. Other examples of a biological fluid include, but are not limited to, saliva, nasopharyngeal, blood, plasma, serum, gastrointestinal fluid, bile, cerebrospinal fluid, pericardial, vaginal fluid, seminal fluid, prostatic fluid, peritoneal fluid, pleural fluid, urine, synovial fluid, interstitial fluid, intracellular fluid or cytoplasm and lymph. bronchial secretions, mucus, or vitreous or aqueous humor. Biological fluid can also include a culture medium. In certain embodiments, a preferred biological fluid is urine.

The disclosure includes methods to provide a sensitive, specific, and noninvasive test for early detection of cancer.

In certain embodiments, the tests use biological samples containing fragmented circulation derived DNA known as "low molecular weight" (LMW) DNA. The DNA is low molecule weight because it is generally less than 300 base pairs in size. This LMW DNA is released into circulation through necrosis or apoptosis by both normal and cancer cells. It has been shown that LWM DNA is excreted into the urine and can be used to detect tumor-derived DNA, provided a suitable assay, such as a short template assay, for detection is available (Su et al. Ann. *NY Acad. Sci.,* 1137:82-91, 2008). Based on the present discovery of how to modify LMW nucleic acid sequences to prevent amplification of the wildtype sequences in a nucleotide amplification reaction assay, LMW DNA from biological samples, for example urine, can be compared to wildtype control DNA with a high degree of specificity.

The modification to the wildtype DNA is made by altering a ribose in the wildtype DNA sequence to provide a template that can be used in standard nucleotide amplification reaction, for example, in PCR assays using commercially available sequence-specific probes and is described in Example 1. The modification results in preventing amplification of the wildtype sequences. Techniques and protocols for performing the assays and analyses are known in the art. For example, melting temperature curve analyses and hybridization guidelines and protocols are well known to those skilled in the art and are found in Innis et al., *PCR Protocols, A Guide to Methods and Applications* (Academic Press, Inc., N.Y., 1990). One such technology is a sequence-specific binding assay using the SIMPLEPROBES™ format (Roche Diagnostics GmbH, Mannheim Germany). These single-labeled probes can detect mutations using a single hybridization probe labeled with one fluorophore to achieve sequence specificity. Typically the probe is designed to specifically hybridize to a target sequence that contains the mutation of interest. Once hybridized to its target sequence, the SIMPLEPROBE™ probe emits more fluorescence than it does when it is not hybridized. Using melting curve analyses in assays comparing mutated p53 249T plasmid DNA to wildtype p53 template DNA, a specificity of 1:1000 of p53 249T DNA to wildtype p53 DNA up was demonstrated. The specificity of screening for a p53 249T mutation compared to a wildtype p53 sequence is described in Examples 4-7.

The present invention has the advantage that the procedures provided are capable of screening for cancers where identifying a mutation in a nucleic acid sequence is particularly significant due to the phenotypic heterogeneity associated with many types of cancer. Some of these cancers have a p53 mutation. The gene sequence for p53 is known (GenBank™ #X54156.) These cancers include hepatocellular carcinoma, colon cancer, breast cancer, lung cancer, prostate cancer, ovarian cancer, bladder cancer, lymphoma and stomach cancer. Of particular concern is hepatocellular carcinoma. Mutations on codon 249T in the p53 gene have been associated with approximately 50% of HCC. Thus, the present invention provides methods of screening for HCC using the p53 249T mutation. When HCC samples were tested using the claimed methods, 11 out of 20 (55%) were detected as positive for p53 mutations by the p53 249T mutation assay in the presence of LNA, and none of the control tissues detected positive. The p53 249T mutation assay was not only able to identify the mutation in the 249 codon, but also detected a mutation occurring in the 248 codon due to the target region of the WT LNA clamp. Thus, the claimed methods can be used for detecting any mutations occurring in the region of the wildtype LNA modification.

The methods described herein can be used to determine the status of existing disease identified in a subject. For example, when 13 urine samples that were positive for p53 mutation were tested, 10 of these samples showed that the detected p53 mutation was undetectable after the HCC was surgically removed. Thus, mutations detected in the urine collected before the surgery can be tested to determine if the status of the patient has changed by evaluating whether LMW nucleic acid with the mutation is no longer detectable in the urine collected after the surgical removal of HCC tumor.

The methods described herein can be used to identify subject patients for treatment and to determine risk factors associated with specific p53-249T associated cancers. Such methods can include, for example, determining whether an individual has relatives who have been diagnosed with a particular disease. Screening methods can also include, for example, conventional work-ups to determine familial status for a particular disease known to have a heritable component. Screening may be implemented as indicated by known patient symptomology, age factors, related risk factors, etc. These methods allow the clinician to routinely select patients in need of the methods described herein for treatment. In accordance with these methods, screening may be implemented as an independent program or as a follow-up, adjunct, or to coordinate with other treatments. Thus, the methods of the present inventions can be used for cancer screening, particularly for early detection, monitoring of recurrence, disease management, and to develop a personalized medicine regime for a cancer patient.

The invention is further illustrated by the following non-limiting examples.

EXAMPLES

Example 1

Preparing Wildtype Locked Nucleic Acid (LNA) Clamp Sequence

Figure 1:
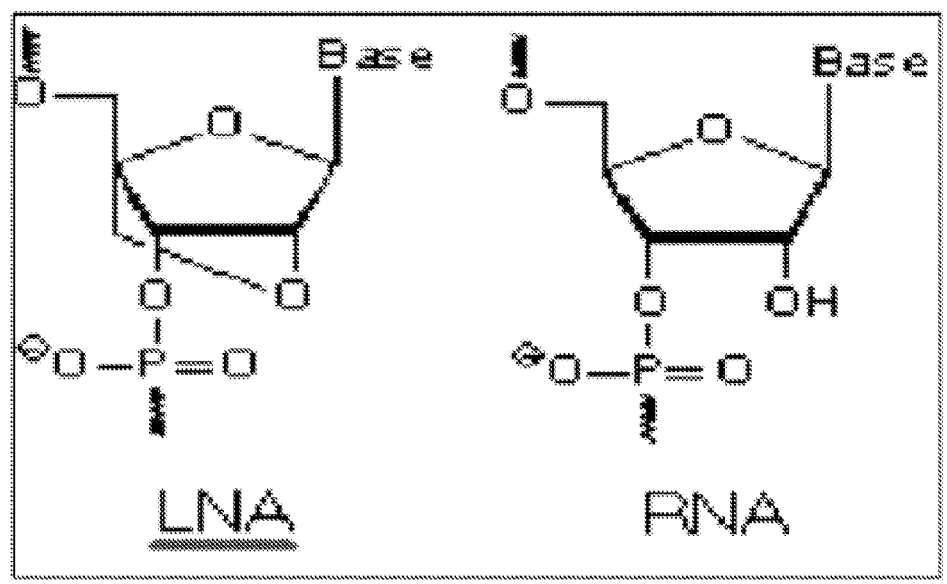
FIG. 1 is a chemical structure drawing illustrating a locked nucleic acid (LNA) and unmodified RNA.

To discriminate between wildtype and mutated p53 sequences a locked nucleic acid (LNA) clamp was designed to inhibit amplification of wildtype DNA in the PCR assay. LNA is a chemically modified RNA nucleotide whose ribose is modified with a methylene bridge connecting the 2'-oxygen and 4'-carbon. This essentially "locks" the ribose in its structural conformation, which provides high thermostability and high affinity recognition to complementary DNA. FIG. 1 is chemical structure representation of the difference between LNA and RNA.

Example 2

PCR Assay Design

A short amplicon was designed for targeting short templates A Locked Nucleic Acid (LNA) Clamp was designed for inhibition of WT amplification as described above. SIMPLEPROBE™ (Roche, Indianapolis, Ind.) was designed for melting curve analysis to identify mutations.

The following LC v2.0 Real-Time PCR Protocol was used: Using Roche LightCycler® 2.0 Real-time PCR instrument assemble a 10 μl reaction using the FastStart DNA Master SYBR® Green I system (Life Technologies, Gaithersburg, Md.). The following reagents were added: in order 5.6 μl of PCR-grade $H_2O$, 1 μl of the 10×SYBR® Green Master Mix (final concentration of 1×), 1.0 μl of 10 μM p53 FwdA and 1.0 μl of 10 μM p53 Rev878 19 primer (final concentration of 1.0 μM), and 0.4 μl of 25 mM $MgCl_2$ (final concentration of 2.0 mM $MgCl_2$). SYBR Green Master Mix already contains 10 mM $MgCl_2$. Mix well and add 9 μl of PCR reaction mix to capillary tube with 1 μl of the respective DNA template for a total of 10 μl reaction volume. Run the PCR reactions in the following conditions: 95° C. for 10 mins, then 95° C. for 64 s. for 20 s, 72° C. for 10 s. for 45 cycles followed by the melting curve at 95° C. for 5 s, 65° C. for 15 s. min, 97° C. for continuous hold. Cooling program is at 40° C. for 30 s. The real-time program provides amplification and melt curve data without any post-PCR handling

TABLE 1

| Primer Name | Primer Region | Primer Length | TM (° C.) | Sequence 5'-3' |
|---|---|---|---|---|
| P53_FwdA | | 19 nt | 66 | ctgcatgggcggcatg (SEQ ID NO: 1) |
| P53_Rev878_19 | | 19 nt | 68 | tgaggatgggcctccggtt (SEQ ID NO: 2) |

TABLE 2

| Primer Name | Primer Region | Primer Length | TM (° C.) | Sequence 5'-3' |
|---|---|---|---|---|
| P53_FwdA | | 19 nt | 66 | ctgcatgggcggcatg (SEQ ID NO: 1) |
| P53Rev_BB | | 15 nt | 55 | tgatggtgaggatgg (SEQ ID NO: 3) |
| 249T mutant SimpleProbe ® | | 12 nt | 64 | accgGaGTccca (SEQ ID NO: 4) |
| 249C2 mutant SimpleProbe ® | | 12 nt | 67 | accgGagCccca (SEQ ID NO: 5) |
| p53 LNA Clamp | | 7 nt | 67 | GGAGGCC (SEQ ID NO: 6) |

*Bold and capitalized based denote locked-nucleic acid bases (LNA)

Example 3

249T Detection Assay PCR

A PCR reaction is performed as follows: Assemble a PCR reaction containing 10 µl total volume in 96-well plate. Using the QIAGEN HotStartPlus DNA Taq® Polymerase system (QIAGEN, Valencia, Calif.) add in order 3.6 µl of DEPC-treated $H_2O$, 1 µl of 10× Buffer (final concentration of 1×), 1 µl of 2.5 mM dNTP (final concentration of 0.25 mM), 0.2 µl of 25 mM $MgCl_2$ (final concentration of 0.5 µM), 1 µl of 10 µM p53FwdA and 1 µl of 10 µM p53Rev B primer (final concentration of 1 µM), 1 µl of 20 µM p53 LNA Clamp (final concentration of 2 µM), 0.2 µl Taq® Polymerase (final concentration of 0.2 U), and 1 µl of DNA template. Place the plastic sealing foil over the 96-well plate and seal well. Centrifuge the 96-well plate briefly before placing in LC480™ Real-time PCR machine. Run reaction at the following PCR amplification conditions: 95° C. for 5 mins, then 95° C. for 30 s., 54° C. for 30 s., 72° C. for 30 s. for 40 cycles followed by elongation at 40° C. for 30 s. Keep PCR products at 4° C. until ready to use.

Melting Curve Reaction is performed as follows: Assemble 249T SIMPLEPROBE™ at the final concentration of 0.2 µM (add 0.67 µl of 3 µM SIMPLEPROBE™ in volume of DEPC-treated $H_2O$ (4.33 ul $H_2O$) to a total of 5 µl. Place reaction mix in a new 96-well plate and add 5 µl of previous PCR reaction for a total of 10 µl. Place the plastic sealing foil over the 96-well plate and seal well. Centrifuge the 96-well plate briefly before placing in LC480™ Real-time PCR machine. Run the melting curve analysis at the following conditions: 95° C. for 10 mins, followed by melting profile of 95° C. for 1 mins, 30° C. for 2 mins, 70° C. for continuous hold. This melting curve analysis will provide PCR product characterization.

Figure 3A:
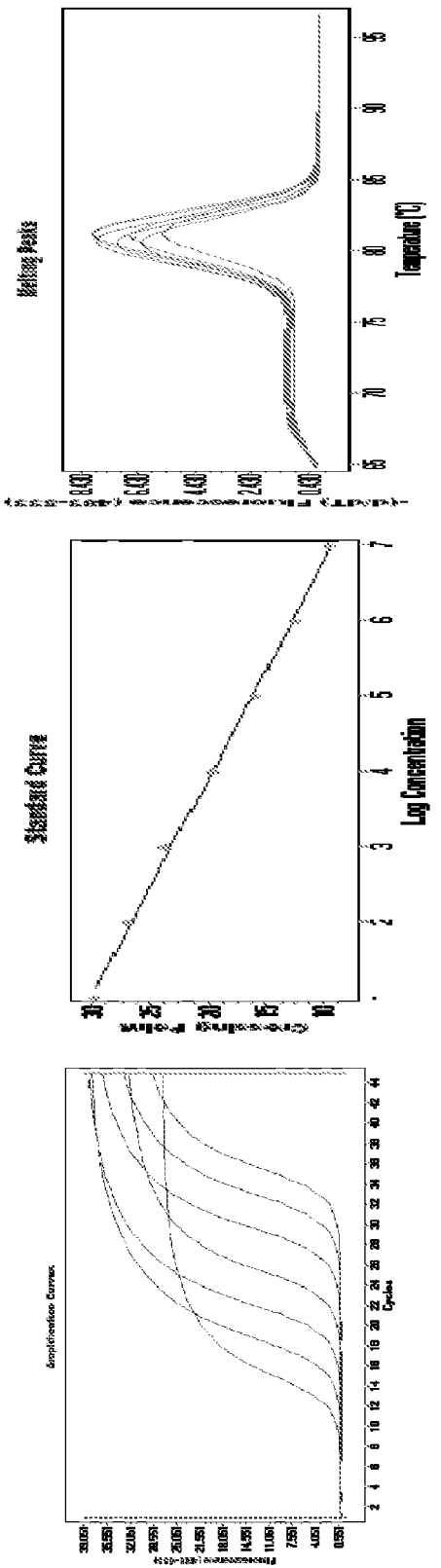
FIG. 3A are graph results from a p53 gene real-time PCR Assay quantifying the p53 gene including codon 249. Graph I) Amplification curves; Graph II) Standard curve; Graph III) Melting curves. The assay generated a linear range from 10 to $10^7$ copies.

FIG. 3A shows the results from a p53 gene real-time PCR assay. A 10-fold serial dilution of plasmid p53 DNA ranging from 1 to $10^7$ copies was used to determine the sensitivity and linearity of the assay. The data are presented as: I) Amplification curves II) Standard curve III) Melting curves. The real-time PCR assay quantified the p53 gene including codon 249. The assay generated a linear range from 10 to $10^7$ copies.

Example 4

Development of p53 249T Mutation Assay

Figure 3B:
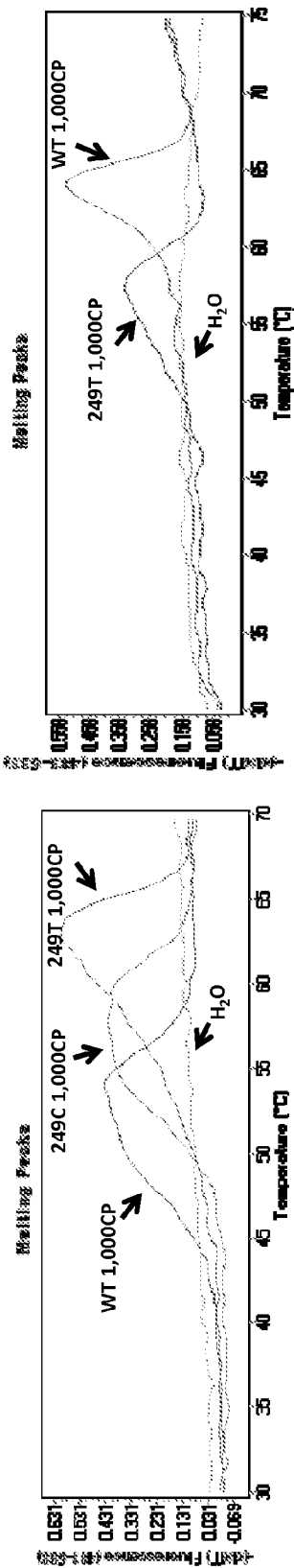
FIG. 3B are graph results of 249T and 249WT SIMPLEPROBE™ Melting Curve Analysis of p53 249 DNA Plasmid DNA standards containing 249T 1,000 copies (CP), 249C 1,000 CP, and WT 1,000 CP were analyzed by melting_curve analysis with (A) 249T specific probe and (B) WT specific_probe. The control is $H_2O$. The 249T SIMPLEPROBE™ distinguished the PCR products generated by mutated templates from WT templates.

A. Assay Development Using p53 249T/C Clone 249T and 249WT SIMPLEPROBE™ Melting Curve Analysis of p53 standards. Plasmid DNA standards 249T 1,000 copies (CP), 249C 1,000 CP, and WT 10,000 CP were subjected to a PCR reaction and the PCR product was subsequently analyzed by melting curve analysis using SIMPLEPROBE™ (A) 249T probe and (B) WT probe. The 249T SIMPLEPROBE™ distinguished the PCR products generated by mutated templates from WT templates. See, FIG. 3B.

Figure 4:
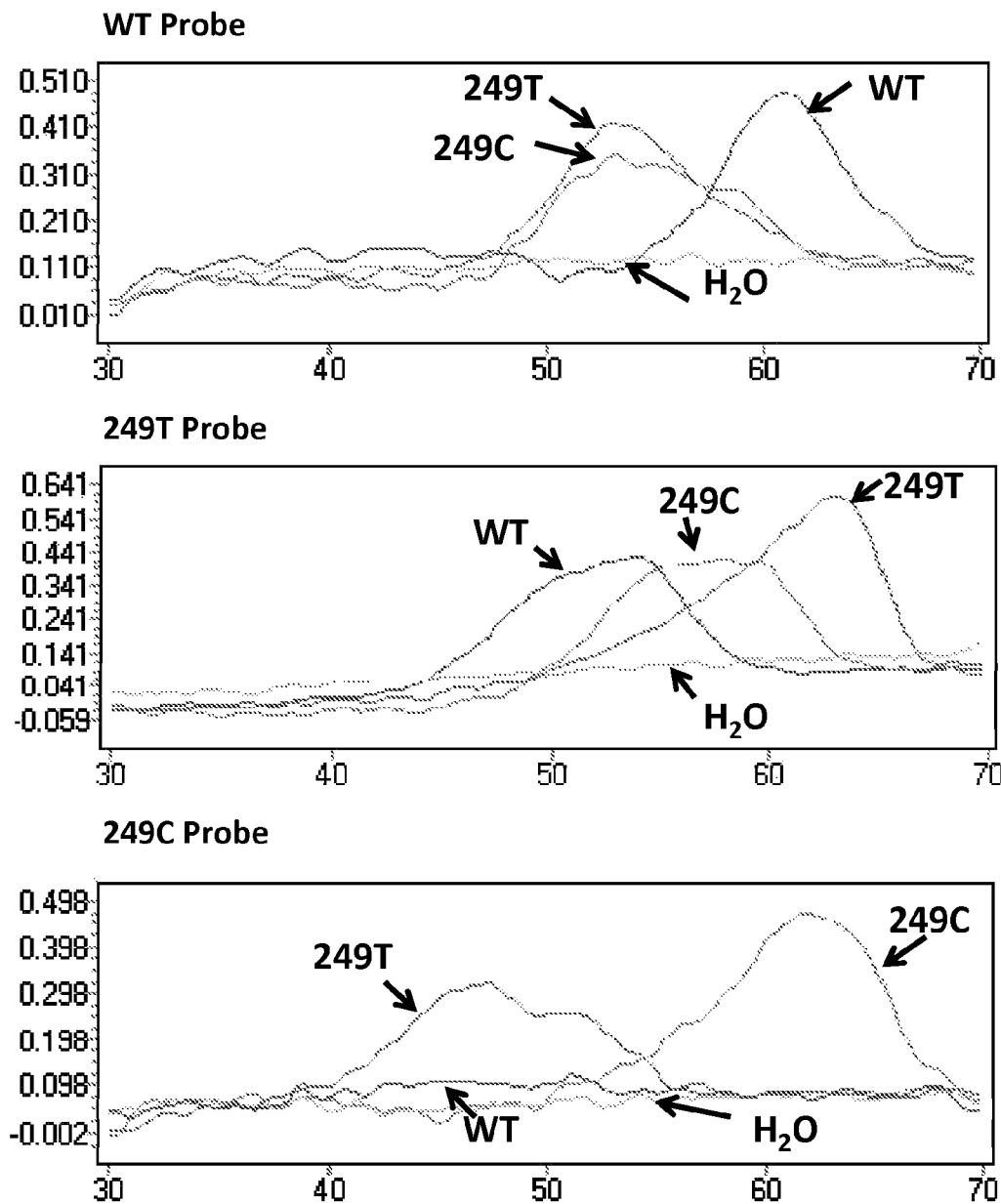
FIG. 4 illustrates PCR products derived from plasmids containing DNA from p53 WT, p53_249T, p53_249C, or $H_2O$ (arrows) were determined by melting curve analysis with the SIMPLEPROBE™ specific for 249WT, 249T, and 249C.

B. p53 249T Mutation Assay Sensitivity is a Single Copy p53 249T mutation assay sensitivity was determined A melting curve analysis of PCR products of 249T Standards 1000 CP to 1 CP using SIMPLEPROBE™ 249T was done. PCR reaction was performed in the presence (+) or absence (−) of WT LNA clamp. The result demonstrated the assay was sensitive enough to detect a single copy. See, FIG. 4A.

C. p53 Mutation Assay Specificity is 1:1000

Figure 5:
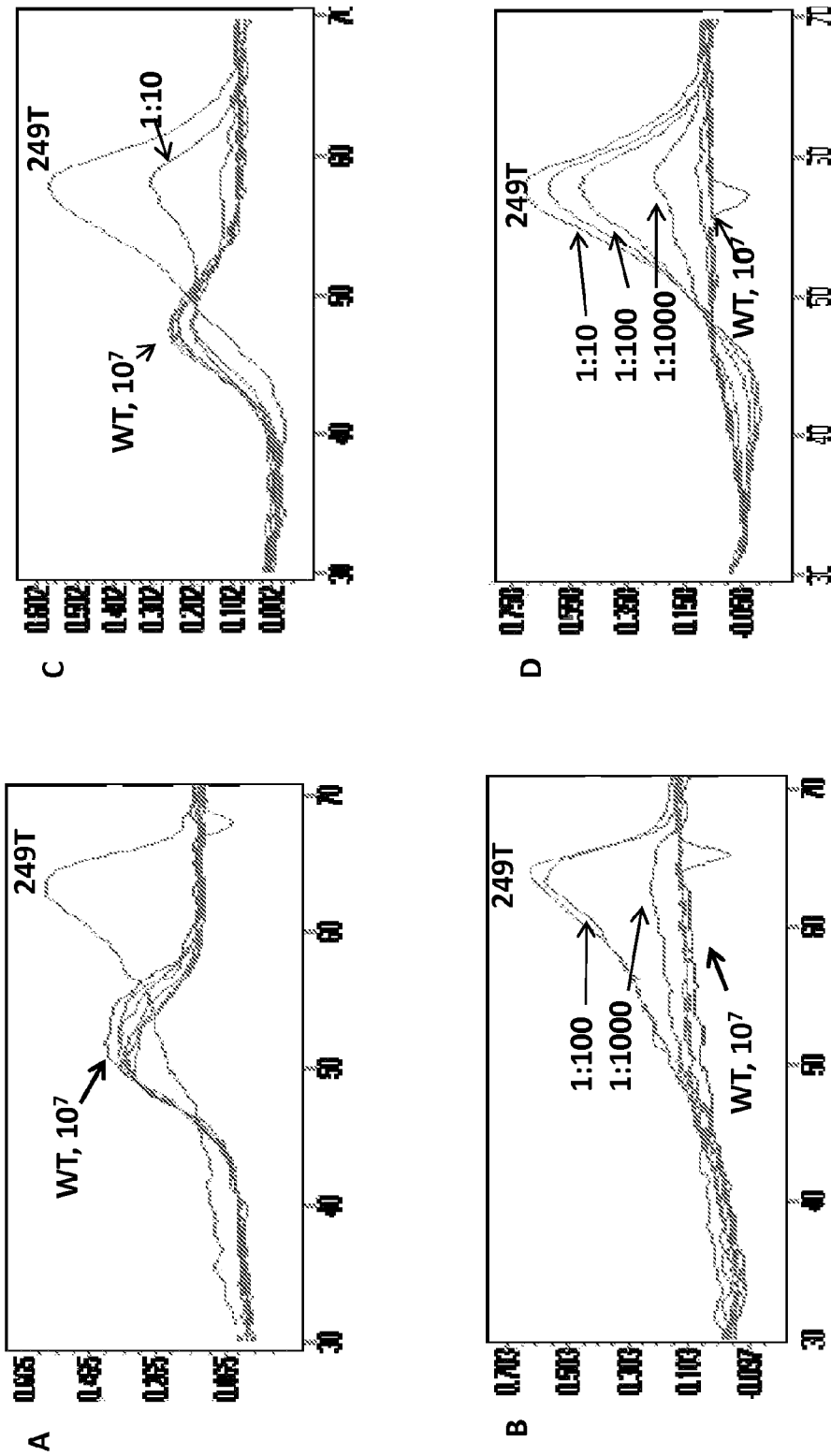

Specificity of the p53 249T mutation assay by using SIMPLEPROBE™ Melting Curve analysis with 249T probe was performed. The specificity of p53 249T mutation assay was determined by (1) reconstitution of 10 CP of plasmid 249T with $10^3$ to $10^7$ CP of WT plasmid in the absence (A) or presence (B) of the WT LNA clamp, (2) 10 to $10^7$ CP of the plasmid 249T was reconstituted with $10^7$ CP of the WT plasmid DNA in the absence (C) or presence (D) of the WT LNA clamp. The specificity of 1:1000 of 249T mutant to WT ratio was obtained. The LNA was able to suppress the amplification of the WT plasmid up to $10^7$ CP. See, FIG. 5.

Example 5 p53 249 Mutation Assay in HCC Tissue

FIG. 6 shows the results of a test p53 249 mutation assay, where 20 pairs of the HCC (K) and its adjacent non-HCC (N) tissues DNA were subjected to the p53 249 mutation assay in the presence (+) and absence (−) of the WT LNA clamp. Examples of melting curve analysis of the positive tissue DNA detected by the p53 249 mutation assay are shown FIGS. 3 and 4. To validate the detection of the p53 249 mutation assay, the PCR products generated in the presence of LNA were cloned into a plasmid and analyzed through DNA sequencing.

FIG. 7 is the DNA sequencing chromatograms showing the mutation site. The results show that 11 out of 20 (55%) HCC samples were detected positive for p53 mutations by the p53 249T mutation assay in the presence of LNA. None of the control tissues were detected as positive for p53 mutation by the assay.

P53 249T mutation assay was validated by DNA sequencing analysis. 3K, 10K, 16K, and 4K 4N (B,C,D,F) displayed the p53 249T mutation while 3K (A) 2K and 18K (A,E) displayed p53 248 related mutations.

P53 249T mutation assay not only identified the mutation in the 249 codon, but also detected the mutation occurring in the 248 codon due to the target region of the WT LNA clamp. This demonstrated the assay was capable of detecting any mutation that occurs in the region of the WT LNA clamp.

Example 6

Detection of p53 249 in Urine of Patients with HCC

FIG. 8 presents the data from a p53 249 mutation assay of 40 HCC LMW DNA sets isolated from urine samples. The samples were collected before (B) and after (A) surgical removal of HCC tumors. As controls, LMW urine DNA isolated from normal (n=13), hepatitis (n=15), and cirrhosis (n=3) were also tested (see FIG. 9). In 18 out of 40 (45%) LMW urine DNA from HCC were positive for p53 mutations.

Out of the 13 (B) and (A) urine sets that were positive for p53 mutation in (B) urine, 10 of these B/A sets showed that the detected p53 mutation was undetectable after the HCC was surgically removed.

What is claimed:

1. A method for detecting hepatocellular carcinoma in a subject comprising:
   amplifying a low molecular weight p53 249T mutation in a urine sample from said subject, wherein the amplification comprises:
   suppressing the amplification of wildtype p53 nucleic acid sequences using a Locked Nucleic Acid clamp formed of GGAGGCC, wherein the Locked Nucleic Acid clamp binds wildtype p53 but not p53 249T nucleic acid sequences, and
   amplifying the sample with primers consisting of SEQ ID NO: 1 and SEQ ID NO: 3; and
   detecting the presence of p53 249T mutant using an oligonucleotide probe, wherein the presence of p53 249T mutant nucleic acid sequences is indicative of hepatocellular carcinoma.

2. The method of claim 1, wherein the low molecular weight p53 249T mutation is a DNA sequence of 50 nucleotides or less.

3. The method of claim 1, wherein the Locked Nucleic Acid clamp is a chemically modified RNA nucleotide having a ribose modified with a methylene bridge connecting a 2'-oxygen and 4'-carbon and wherein the Locked Nucleic Acid clamp is complementary to wild type p53.

4. The method of claim 1, comprising an additional first step of isolating a low molecular weight nucleic acid from the biological sample prior to amplifying and detecting the presence of p53 249T.

5. A kit for detecting a circulating LMW p53 249T mutant DNA sequence in a urine sample from a patient being tested for hepatocellular carcinoma comprising (a) a LNA clamp formed of GGAGGCC; (b) primers to amplify a DNA sequence encoding for codons 248-250 of p53, wherein said primers consist of SEQ ID NO: 1 and SEQ ID NO: 3; and (c) a Fluorescein-labeled p53 249T oligonucleotide probe, wherein the probe specifically hybridizes to a p53 249T mutant sequence and emits more fluorescence than it does when it is not hybridized to the p53 249T mutant.

6. The kit of claim 5, wherein (c) consists of SEQ ID NO: 4 and SEQ ID NO: 5.

7. The method of claim 1, wherein the absence of p53 249T mutant nucleic acid sequences is indicative of an absence of hepatocellular carcinoma.

\* \* \* \* \*

SEQUENCE LISTING

```
<160> NUMBER OF SEQ ID NOS: 8

<210> SEQ ID NO 1
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
ctgcatgggc ggcatg                                                    16

<210> SEQ ID NO 2
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
tgaggatggg cctccggtt                                                 19

<210> SEQ ID NO 3
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
tgatggtgag gatgg                                                     15

<210> SEQ ID NO 4
<211> LENGTH: 12
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (5)..(5)
<223> OTHER INFORMATION: LNA
<220> FEATURE:
<221> NAME/KEY: modified_base
<222> LOCATION: (7)..(8)
```

```
<223> OTHER INFORMATION: LNA

<400> SEQUENCE: 4
accggagtcc ca                                                           12

<210> SEQ ID NO 5
<211> LENGTH: 12
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (5)..(5)
<223> OTHER INFORMATION: LNA
<220> FEATURE:
<221> NAME/KEY: modified_base
<222> LOCATION: (8)..(8)
<223> OTHER INFORMATION: LNA

<400> SEQUENCE: 5
accggagccc ca                                                           12

<210> SEQ ID NO 6
<211> LENGTH: 7
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6 ggaggcc                                                                  7

<210> SEQ ID NO 7
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
tcctgcatgg gcggcatgaa ccggaggccc atcctcacca tcatcacact ggaagactcc        60

<210> SEQ ID NO 8
<211> LENGTH: 12
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
accggaggcc ca                                                           12
```